(12) United States Patent
Miyano et al.

(10) Patent No.: US 10,980,826 B2
(45) Date of Patent: Apr. 20, 2021

(54) PHARMACEUTICAL COMPOSITION FOR TREATING AND/OR PREVENTING CANCER

(71) Applicant: TORAY INDUSTRIES, INC., Tokyo (JP)

(72) Inventors: Atsuko Miyano, Kamakura (JP); Hiroko Sudo, Kamakura (JP); Aiko Takayama, Kamakura (JP); Taiga Arai, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 158 days.

(21) Appl. No.: 15/772,751

(22) PCT Filed: Nov. 2, 2016

(86) PCT No.: PCT/JP2016/082670
§ 371 (c)(1),
(2) Date: May 30, 2018

(87) PCT Pub. No.: WO2017/078099
PCT Pub. Date: May 11, 2017

(65) Prior Publication Data
US 2019/0216839 A1 Jul. 18, 2019

(30) Foreign Application Priority Data
Nov. 6, 2015 (JP) .............................. JP2015-218358

(51) Int. Cl.
| | | |
|---|---|---|
| *A61K 48/00* | (2006.01) | |
| *C07H 21/04* | (2006.01) | |
| *A61K 31/7088* | (2006.01) | |
| *A61K 31/7105* | (2006.01) | |
| *A61K 31/713* | (2006.01) | |
| *A61K 45/00* | (2006.01) | |
| *C12N 15/113* | (2010.01) | |
| *A61P 35/02* | (2006.01) | |
| *A61K 45/06* | (2006.01) | |

(52) U.S. Cl.
CPC ........ *A61K 31/7088* (2013.01); *A61K 31/713* (2013.01); *A61K 31/7105* (2013.01); *A61K 45/00* (2013.01); *A61K 48/00* (2013.01); *A61P 35/02* (2018.01); *C12N 15/113* (2013.01); *A61K 45/06* (2013.01); *C12N 2310/141* (2013.01); *C12N 2320/30* (2013.01)

(58) Field of Classification Search
CPC . A61K 31/713; C12N 15/113; C12N 2310/11
See application file for complete search history.

(56) References Cited

U.S. PATENT DOCUMENTS

| | | | | |
|---|---|---|---|---|
| 7,507,792 B2 * | 3/2009 | Fisher | ................ | G01N 33/5743 530/350 |
| 8,889,649 B2 | 11/2014 | Nakashiro et al. | | |
| 2012/0277284 A1 | 11/2012 | Swayze et al. | | |

FOREIGN PATENT DOCUMENTS

| | | | | |
|---|---|---|---|---|
| JP | 2013-504542 A | 2/2013 | | |
| JP | 2014-511686 A | 5/2014 | | |
| WO | WO 2004/069991 A2 * | 8/2004 | ........... | C12N 15/113 |
| WO | WO 2011/029903 A1 | 3/2011 | | |
| WO | WO 2012/135736 A2 * | 10/2012 | ........... | C12N 15/113 |
| WO | WO 2014/071205 A1 | 5/2014 | | |
| WO | WO 2014/072468 A1 | 5/2014 | | |
| WO | WO 2014/199377 A1 * | 12/2014 | ........... | C12N 15/113 |

OTHER PUBLICATIONS

International Search Report, issued in PCT/JP2016/082670, dated Dec. 13, 2016.
Kojima et al., "MicroRNA Markers for the Diagnosis of Pancreatic and Biliary-Tract Cancers", PLoS One, Feb. 23, 2015, vol. 10, No. 2 , pp. 1-22, see Table 2.
Written Opinion of the International Searching Authority, issued in PCT/JP2016/082670, dated Dec. 13, 2016.
Baker et al., "Human micro RNA (miR-6808), SEQ 2600." Database Geneseq (Online), Accession No. BBJ07465 standard; RNA; 22 BP., XP-002791759, Aug. 14, 2014, 2 pages.
Baker et al., "Human micro RNA (miR-6876), SEQ 2664.," Database Geneseq (Online), Accession No. BBJ07529, XP-002791760, Aug. 14, 2014, 2 pages.
Baker et al., "Human micro RNA (miR-6893), SEQ 2681.," Database Geneseq (Online), Accession No. BBJ07546, XP-002791757, 2 pages.
Extended European Search Report, dated Jun. 17, 2019, for European Application No. 16862159.7.
Hoge et al., "Human hsa-miR-4476 microRNA, SEQ ID 4556.," Database Geneseq (Online), Accession No. BBK86002, XP-002791758, Sep. 11, 2014, 1 page.
European Office Action issued in Application No. 16862159.7 dated Jun. 5, 2020.
Zhang et al., "microRNAs as oncogenes and tumor suppressors", Developmental Biology, Elsevier, vol. 302, 2007, pp. 1-12.
Hino at al., "RNAi for drug discovery and medical application," Journal of Clinical and Experimental Medicine, vol. 208, No. 8, 2004, pp. 653-658, 7 pages total, with an English translation.
Japanese Office Action for Japanese Application No. 2017-524484, dated Oct. 6, 2020.

* cited by examiner

*Primary Examiner* — Amy H Bowman
(74) *Attorney, Agent, or Firm* — Birch, Stewart, Kolasch & Birch, LLP

(57) ABSTRACT

The present application provides a pharmaceutical composition for treating and/or preventing a cancer comprising, as an active ingredient, a polynucleotide derived from miRNA associated with the cancer, a combination drug of the pharmaceutical composition and another antitumor agent, and a method for treating or preventing a cancer in a subject having the cancer using the pharmaceutical composition or the combination drug.

7 Claims, 11 Drawing Sheets

Specification includes a Sequence Listing.

PHARMACEUTICAL COMPOSITION FOR TREATING AND/OR PREVENTING CANCER

TECHNICAL FIELD

The present invention relates to a pharmaceutical composition for treating and/or preventing a cancer comprising, as an active ingredient, a polynucleotide derived from a microRNA.

BACKGROUND ART

MicroRNA (miRNA) is a RNA of 16-28 nucleotides that is not translated into a protein, and it is currently known that 2590 miRNAs are present in human according to the miRBase release 21 (http://www.mirbase.org/). In recent years, miRNAs have been receiving attention as the molecule for suppressing in vivo expression of various genes. On the genome, a region of each miRNA gene is present and is transcribed into a RNA precursor with hairpin structure following the action of RNA polymerase II, which precursor is then cleaved by 2 types of dsRNA cleaving enzymes having RNase III cleavage activities that are called Drosha in the nuclear and Dicer in the cytoplasm, thereby forming a mature miRNA. It is known that the mature miRNA is taken into the protein complex called RISC and interacts with mRNAs of a plurality of target genes having complementary sequences to suppress the expression of a gene (Non Patent Literature 1).

A certain type of miRNAs is suggested to be associated with human diseases including cancers, and particularly in cancers, for examples, many miRNAs such as hsa-miR-6893-5p, hsa-miR-4476 and hsa-miR-575 are known to become a marker specific to pancreatic cancers in blood (Non Patent Literature 1).

Further, in addition to the miRNAs associated with the growth of cancer cells, the presence of a miRNA which works in a direction of suppressing cancer cells is reported, suggesting a method for treating cancers utilizing the expression pattern of the miRNA. Specific examples of the known method include a method for treating diseases such as cancers by administering an activated serum comprising 153 miRNAs such as hsa-Let-7a and upregulating the miRNA (Patent Literature 1), a method for treating a lung cancer using a body fluid comprising many miRNAs such as hsa-Let-7a (Patent Literature 2), and a method for treating a blood cancer by administering antisense oligonucleotides of many miRNAs such as miR-1321 comprised in circulating exosomes in the body (Patent Literature 3).

PRIOR ART LITERATURE

Patent Literature

Patent Literature 1: JP Patent Publication (Kohyo) No. 2013-504542
Patent Literature 2: International Publication No. WO 2014/072468
Patent Literature 3: International Publication No. WO 2014/071205

Non Patent Literature

Non Patent Literature 1: Kojima M PLoS One. 10(2) (2015) "MicroRNA markers for the diagnosis of pancreatic and biliary-tract cancers"

SUMMARY OF INVENTION

Problem to be Solved by Invention

It is an object of the present invention to identify a miRNA exhibiting a therapeutic and/or preventive effect in common on various types of cancers among various cancer-relating miRNAs, and to provide a novel pharmaceutical composition for treating and/or preventing a cancer comprising, as an active ingredient, a polynucleotide derived from the miRNA.

Means for Solution of Problem

The present inventors conducted extensive studies to solve the above-mentioned problem and have now found novel polynucleotides which suppress the growth of cancer cells among miRNAs with increased or decreased expression in body fluids or tissues of cancer patients, whereby the present invention was accomplished.

More specifically, the present invention has the following features (1) to (14).

(1) A pharmaceutical composition for treating and/or preventing a cancer, comprising, as an active ingredient, a polynucleotide comprising the nucleotide sequence represented by SEQ ID NO: 1 or 2.
(2) The pharmaceutical composition according to (1), wherein the polynucleotide is 8-60 nucleotides in length.
(3) The pharmaceutical composition according to (1) or (2), wherein the polynucleotide comprises a nucleotide sequence of the following (a) or (b) at the 3' terminal side of the nucleotide sequence represented by SEQ ID NO: 1 or 2:
(a) a nucleotide sequence represented by any of SEQ ID NOs: 3 to 6 and 16; or
(b) a nucleotide sequence comprising a deletion(s), substitution(s), insertion(s) and/or addition(s) of 1-5 nucleotides in the nucleotide sequence represented by any of SEQ ID NOs: 3 to 6 and 16.
(4) The pharmaceutical composition according to any one of (1) to (3), wherein the polynucleotide comprises a nucleotide sequence represented by any of SEQ ID NOs: 7 to 10, 12 and 13.
(5) The pharmaceutical composition according to any one of (1) to (4), wherein the polynucleotide is single stranded or double stranded.
(6) The pharmaceutical composition according to any one of (1) to (5), wherein the polynucleotide is RNA.
(7) The pharmaceutical composition according to any one of (1) to (6), wherein the cancer is a solid cancer.
(8) The pharmaceutical composition according to (7), wherein the solid cancer is selected from the group consisting of breast cancer, kidney cancer, pancreatic cancer, colorectal cancer, lung cancer, brain tumor, stomach cancer, cervical cancer, ovarian cancer, prostate cancer, bladder cancer, esophagus cancer, liver cancer, fibrosarcoma, mast cell tumor, and melanoma.
(9) The pharmaceutical composition according to any one of (1) to (6), wherein the cancer is a blood cancer.
(10) The pharmaceutical composition according to (9), wherein the blood cancer is leukemia.
(11) The pharmaceutical composition according to any one of (1) to (10), wherein the polynucleotide is inserted expressively in a vector in the form of DNA.
(12) The pharmaceutical composition according to any one of (1) to (11), wherein the polynucleotide is encapsulated (or included) in a carrier selected from the group consisting of non-cationic polymer carriers, liposome carriers, dendritic carriers, nano-material carriers, microparticle carriers, biostructural carriers, micelle carriers, polymer microparticles, and magnetic fine particles, or is bound thereto.

(13) A combination drug for treating and/or preventing a cancer comprising, as active ingredients, the pharmaceutical composition according to any one of (1) to (12) and an antitumor agent.

(14) A method for treating or preventing a cancer in a subject who suffers or has suffered from the cancer, comprising administering the pharmaceutical composition according to any one of (1) to (12), or the combination drug according to (13) to the subject.

The pharmaceutical composition for treating and/or preventing cancers of the present invention notably suppresses the growth of cancer cells of various cancer types, and thus is useful for treating and preventing cancers.

The present description includes the contents disclosed in Japanese Patent Application No. 2015-218358 from which the present application claims the priority.

MODE FOR CARRYING OUT INVENTION

Figure 1:
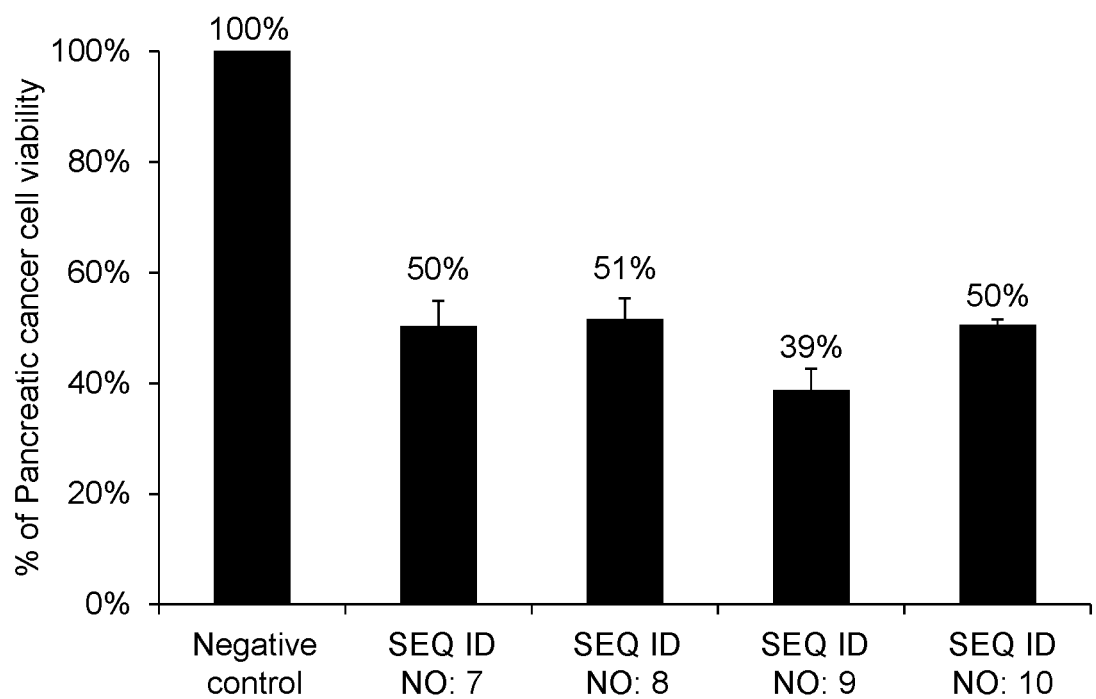
FIG. 1 shows percentages, relative to the viable cell count (100%) of pancreatic cancer cell line Panc-1 after transferring the negative control oligo as a synthetic RNA, of the viable cell counts after transferring a synthetic RNA having the same nucleotide sequence as hsa-miR-6893-5p represented by SEQ ID NO: 7, a synthetic RNA having the same nucleotide sequence as hsa-miR-4476 represented by SEQ ID NO: 8, a synthetic RNA having the same nucleotide sequence as hsa-miR-6808-5p represented by SEQ ID NO: 9, and a synthetic RNA having the same nucleotide sequence as hsa-miR-6876-5p represented by SEQ ID NO: 10.

The present invention will be described in more detail.
<Polynucleotide as Active Ingredient>

The pharmaceutical composition for treating and/or preventing a cancer of the present invention comprises, as an active ingredient, a polynucleotide comprising the nucleotide sequence represented by CAGGCAGG (SEQ ID NO: 1) or CAGGAAGG (SEQ ID NO: 2). Hereinafter, the polynucleotide to be the active ingredient is described.

The nucleotide sequence represented by SEQ ID NO: 1 is the nucleotide sequence identified as a partial sequence at the 5' terminal side of hsa-miR-6893-5p (miRBase Accession No. MIMAT0027686), which is a human miRNA. Additionally, the nucleotide sequence represented by SEQ ID NO: 2 is the nucleotide sequence identified as a partial sequence at the 5' terminal side of hsa-miR-4476 (miRBase Accession No. MIMAT0019003), which is a human miRNA. These miRNAs are known as parts of the miRNAs that are markers specific to pancreatic cancer (Kojima M PLoS One. 10(2) (2015) "MicroRNA markers for the diagnosis of pancreatic and biliary-tract cancers"); however, it has been newly found by the present inventors that they suppress the growth of cells of pancreatic cancer and other cancers and that the polynucleotide of the nucleotide sequence represented by SEQ ID NO: 1 or 2, which is a partial sequence of these miRNAs, plays an important role in suppressing cancer cell growth.

Thus, the polynucleotide described above is not limited as long as it comprises the nucleotide sequence represented by SEQ ID NO: 1 or 2. More specifically, the nucleotide sequence represented by SEQ ID NO: 1 or 2 may be the polynucleotide itself, or a different nucleotide sequence may be added at the 5' terminal side or 3' terminal side of the nucleotide sequence represented by SEQ ID NO: 1 or 2, and the polynucleotide with a different nucleotide sequence added at the 3' terminal side of the nucleotide sequence represented by SEQ ID NO: 1 or 2 is preferred. Further, the polynucleotide is preferably 8-60 nucleotides in length, more preferably 16-28 nucleotides in length.

The nucleotide sequence to be added at 3' terminal side of the nucleotide sequence represented by SEQ ID NO: 1 or 2 is preferably a nucleotide sequence comprising the following (a) or (b) as a partial sequence, more preferably a nucleotide sequence comprising the following (a) or (b) at the 5' terminal side, and far more preferably a nucleotide sequence consisting of the following (a) or (b):
(a) a nucleotide sequence represented by any of SEQ ID NOs: 3 to 6 and 16; or
(b) a nucleotide sequence comprising a deletion(s), substitution(s), insertion(s) and/or addition(s) of 1-5 nucleotides, preferably 1-4 nucleotides, more preferably 1-3 nucleotides, far more preferably 1-2 nucleotides, and particularly preferably 1 nucleotide, in the nucleotide sequence represented by any of SEQ ID NOs: 3 to 6 and 16.

Examples of the preferable polynucleotide with a different nucleotide sequence added at the 3' terminal side of the nucleotide sequence represented by SEQ ID NO: 1 or 2 include polynucleotides, each of which consists of the nucleotide sequence represented by any of SEQ ID NOs: 7 to 10, 12 and 13. Of the 6 polynucleotides, the polynucleotides that comprise the nucleotide sequences represented by any of SEQ IDs NO: 7 to 10 are known as the miRNAs already identified in human. Names and miRBase Accession Nos. (registration numbers) of these miRNAs are as shown in Table 1.

TABLE 1

| SEQ ID NO. | Gene Name | miRBase Accession No. |
|---|---|---|
| 7 | hsa-miR-6893-5p | MIMAT0027686 |
| 8 | hsa-miR-4476 | MIMAT0019003 |
| 9 | hsa-miR-6808-5p | MIMAT0027516 |
| 10 | hsa-miR-6876-5p | MIMAT0027652 |
| 11 | hsa-miR-4454 | MIMAT0018976 |
| 14 | hsa-miR-575 | MIMAT0003240 |
| 15 | hsa-miR-1321 | MIMAT0005952 |

The hsa-miR-6893-5p, which is a miRNA having the nucleotide sequence represented by SEQ ID NO: 7, is composed of the nucleotide sequence represented by SEQ ID NO: 1, which is the nucleotide sequence of from the 5' terminal nucleotide to the 8th nucleotide of SEQ ID NO: 7, and the nucleotide sequence represented by SEQ ID NO: 3, which is the nucleotide sequence of from the 9th nucleotide to the 3' terminal nucleotide of SEQ ID NO: 7. As described above, the miRNA is known to be a marker specific to pancreatic cancers but it has not been reported that compounds obtained using the sequence of the gene or the transcript thereof can suppress tumor cells.

The hsa-miR-4476, which is a miRNA having the nucleotide sequence represented by SEQ ID NO: 8, is composed of the nucleotide sequence represented by SEQ ID NO: 2, which is the nucleotide sequence of from the 5' terminal nucleotide to the 8th nucleotide of SEQ ID NO: 8, and the nucleotide sequence represented by SEQ ID NO: 4, which is the nucleotide sequence of from the 9th to the 3' terminal nucleotide of SEQ ID NO: 8. The miRNA was identified by the method described by Jima D D et al., 2010, Blood, vol. 116, p. 118-127. Additionally, the precursor of the hsa-miR-4476 is known as, hsa-mir-4476 (miRBase Accession No. MI0016828), which has a hairpin-like structure, but it has not been reported that compounds obtained using the sequence of the gene or the transcript thereof can suppress tumor cells.

The hsa-miR-6808-5p, which is a miRNA having the nucleotide sequence represented by SEQ ID NO: 9, is composed of the nucleotide sequence represented by SEQ ID NO: 1, which is the nucleotide sequence of from the 5' terminal nucleotide to the 8th nucleotide of SEQ ID NO: 9, and the nucleotide sequence represented by SEQ ID NO: 5, which is the nucleotide sequence of from the 9th nucleotide to the 3' terminal nucleotide of SEQ ID NO: 9. The miRNA was identified by the method described by Ladewig E et al., 2012, Genome Res., Vol. 22, p. 1634-1645. Additionally, the precursor of the hsa-miR-6808-5p is known as hsa-mir-6808-5p (miRBase Accession No. MI0022653), which has a hairpin-like structure, but it has not been reported that compounds obtained using the sequence of the gene or the transcript thereof can suppress tumor cells.

The hsa-miR-6876-5p, which is a miRNA having the nucleotide sequence represented by SEQ ID NO: 10, is composed of the nucleotide sequence represented by SEQ ID NO: 2, which is the nucleotide sequence of from the 5' terminal nucleotide to the 8th nucleotide of SEQ ID NO: 10, and the nucleotide sequence represented by SEQ ID NO: 6, which is the nucleotide sequence of from the 9th nucleotide to the 3' terminal nucleotide of SEQ ID NO: 10. The miRNA was identified by the method described by Ladewig E et al., 2012, Genome Res., Vol. 22, p. 1634-1645. Additionally, the precursor of the hsa-miR-6876-5p is known as hsa-mir-6876-5p (miRBase Accession No. MI0022723), which has a hairpin-like structure, but it has not been reported that compounds obtained using the sequence of the gene or the transcript thereof can suppress tumor cells.

On the other hand, the polynucleotide comprising the nucleotide sequence represented by SEQ ID NO: 12 is an artificial polynucleotide wherein the nucleotide sequence of SEQ ID NO: 16, which is the nucleotide sequence of from the 9th nucleotide to the 3' terminal nucleotide, from the 5' terminal side, of hsa-miR-4454 (Kojima M PLoS One. 10(2) (2015) "MicroRNA markers for the diagnosis of pancreatic and biliary-tract cancers") that is a miRNA having the nucleotide sequence represented by SEQ ID NO: 11 known as a cancer marker but not known to suppress tumor cells, is fused to the 3' terminal side of the nucleotide sequence represented by SEQ ID NO: 2. Similarly, the polynucleotide comprising the nucleotide sequence represented by SEQ ID NO: 13 is an artificial polynucleotide wherein the nucleotide sequence of SEQ ID NO: 3, which is the nucleotide sequence of from the 9th nucleotide to the 3' terminal nucleotide, from the 5' terminal side, of the above hsa-miR-6893-5p (SEQ ID NO: 7) is fused to the 3' terminal side of nucleotide sequence represented by SEQ ID NO: 2.

The above-mentioned polynucleotides may have any structures as long as they exhibit the effect to treat and/or prevent cancers, and, for example, may have a single stranded structure, a double stranded structure, or a multiple stranded structure having 3 or more strands, preferably a single stranded or double stranded structure, more preferably a single stranded structure.

The above-mentioned polynucleotides may be RNA, DNA or RNA/DNA (chimera), as long as they exhibit the effect to treat and/or prevent cancers (with regard to the polynucleotides, when the entire or partial nucleotide sequences corresponding to the nucleotide sequence described in Sequence Listing are DNA, U (uracil) in Sequence Listing is to be replaced with T (thymine)), but RNA is preferable. Examples of the RNA include, from the viewpoint of regulating genes associated with the suppression of tumor cells, RNA forms such as mRNA, rRNA, non-coding RNA, siRNA, shRNA, snoRNA, snRNA, nkRNA (registered tradename), and PnkRNA (tradename), in addition to the miRNAs described above, preferably miRNAs. The miRNAs include, in addition to naturally occurring miRNAs, synthetic miRNAs, which are so-called mimics.

The polynucleotides usable in the present invention can comprise at least one modified nucleotide analog. The nucleotide analog, for example, can be placed at the 5' end of a RNA molecule, 3' end of a RNA molecule, and/or inside a RNA molecule. Particularly, where the modified nucleotide analog is incorporated, the polynucleotide can be stabilized.

The nucleotide analog is preferably a sugar- or backbone-modified ribonucleotide, and more preferably a ribonucleotide having a modified nucleic acid base, more specifically, a ribonucleotide comprising a non-naturally occurring nucleic acid base. In other words, the non-naturally occurring nucleic acid bases are uridine or cytidine modified at position 5, such as 5-methyluridine, 5-(2-amino)propyluridine, 5-methyl-2-thiouridine or 5-bromouridine, 6-azouridine, adenosine and guanosine modified at position 8 such as 8-bromoguanosine, deazanucleotide, 7-deaza-adenosine; O- and N-alkylated nucleotides, N6-methyladenosine, and universal base.

Preferable sugar-modified ribonucleotides may have the 2'OH group substituted with a group selected from the group consisting of H, OR, halo, SH, SR, $NH_2$, NHR, $NR_2$ and CN, or may comprise a 2'-O, 4'-C methylene bridge or ethylene bridge (for example, LNA and ENA), wherein R is C1-C6 alkyl, alkenyl or alkynyl, and halo is F, Cl, Br or I. Further, the sugar moiety may be mannose, arabinose, glucopyranose, galactopyranose, 4'-thioribose or other sugars, a hetero ring or a carbon ring.

Preferable backbone-modified ribonucleotides have substitutions of, for example, a phosphothioate group, as a modifying group, or boranophosphate, 3'-(or 5'-)deoxy-3'-(or 5'-)aminophosphoramidate, hydrogen phosphonate, boranophosphate ester, phosphoramidate, alkyl or aryl phosphonate and phosphotriester or a phosphorus bond, for the phosphoester group that binds an adjacent ribonucleotide. The modifications described above may be in combination.

<Carrier to be Added to the Active Ingredient Polynucleotide>

The pharmaceutical composition for treating and/or preventing cancers of the present invention may comprise a pharmaceutically acceptable carrier in addition to the above-described polynucleotide. The pharmaceutically acceptable carrier is preferably a substance which facilitates the selective transport of the polynucleotide to target cancer cells or cancer tissues, does not stimulate the living body, and does not inhibit the activities and properties of the polynucleotide, and it is also preferable that the carrier itself does not induce the production of harmful antibodies to individuals to which the composition is administered. The size of carrier is preferably a size which does not permeate normal vessel walls but can permeate newborn blood vessels in cancer tissues. When the carrier is an approximate spheroid, the diameter of the carrier may be preferably a nano size of, for example, about 1 nm or more and less than 1000 nm.

The carrier may encapsulate (or include) the polynucleotide or may movably bind to the polynucleotide. The "movably bind" refers to the electronic interaction between the carrier and one or more agents. The interaction is not limited and may be in the form of chemical bonds including covalent bond, polar covalent bond, ionic bond, electrostatic coupling, coordinate covalent bond, aromatic bond, hydrogen bond, or dipole or Van der Waals interaction.

The binding site of the polynucleotide with the carrier is preferably at the 5' terminal side or 3' terminal side, more preferably the 5' terminal side.

Examples of the carrier include non-cationic polymer carriers, liposome carriers, dendritic carriers, nano-material carriers, microparticle carriers, biostructural carriers, micelle carriers, polymer microparticles, and magnetic fine particles.

The non-cationic polymer carrier may encapsulate (or include) one or more agents and/or movably bind to one or more agents, and may be, for example, an anionic (i.e., negatively charged) polymer or an electronically neutral cotton-like or branched polymer. The carrier may be in the form of microparticles or nanoparticles, or water-soluble or water-insoluble, or biodegradable or non-biodegradable.

Preferable non-cationic polymer carriers are known by those skilled in the art and include, for example, poly-L-glutamic acid (PGA), poly-(γ-L-glutamyl glutamine) (PGGA), poly-(γ-L-aspartyl glutamine) (PGAA), poly-(lactide-co-glycolide) (PLGA), and a mixture of at least 2 polymers.

The liposome carrier may include a single lipid double layer (or unilamellar) or a concentric lipid double layer consisting of 2 or more layers (or multilamellar), which has a lipid double layer structure comprising lipids attached to polar hydrophilic groups and forming, in an aqueous medium, a substantially closed structure which may encapsulate (or include) one or more agents and/or may movably bind one or more agents. The liposome carrier may be in the shape of approximate spherical or approximate elliptical. Preferable liposome carriers are known by those skilled in the art, and can be selected based on various properties such as the rigidity of the lipid double layer, the electronic charge of the lipid double layer and/or the compatibility of one or both of the agents with the liposome carrier. Examples of lipids include natural phospholipids such as egg phosphatidylcholine, egg phosphatidylethanolamine, soy phosphatidylcholine, lecithin and sphingomyelin, synthetic phosphatidylcholine, lysophosphatidylcholine, phosphatidylglycerol, phosphatidic acid, phosphatidyl ethanolamine, dioctadecylamide glycylspermine, dioleoylphosphatidylethanolamine, N-[1-(2,3-dioleyloxy)propyl]-N,N,N-trimethylammoniumchloride, 2,3-diolexyoloxy-N-[2-(sperminecarboxamido)ethyl]-N,N-dimethyl-1-propaneammonium trifluoroacetamide, phosphatidylserine, and derivatives thereof, and PEGylated phospholipids.

The dendritic carrier may be, for example, a dendrimer, a dendron, or derivatives thereof, which may encapsulate (or include) one or more agents and/or may movably bind to one or more agents. The dendrimer is a macromolecule having a core and a plurality of branch-structured shells spreading from the core. The dendron is a type of dendrimer having branches spreading from a focal point. The dendritic carriers are commercially available or can be synthesized by known methods by those skilled in the art. The dendritic carrier may be partly hydrophobic or hydrophilic. The dendritic carrier may be cationic, electronically neutral or anionic. The dendritic carrier may comprise a core molecule, and its examples include alkyl diamines such as ethylenediamine, 1,4-diaminobutane, 1,6-diaminohexane and 1,12-diaminodecane; amines such as ammonia; alkylimines such as cystamine and polyethyleneimine (PEI); chlorinated phosphorus molecules such as cyclotriphosphazene and thiophosphoryl. Additionally, polyalkylimines such as polypropyleneimine (PPI) and DAB-Am-16; tertiary amines such as polyamideamine (PAMAM); polyamino acids such as polylysine; and phenoxymethyl (methylhydrazono) (PMMH) may also be comprised.

The nano-material carrier may be a material having, for example, the longest dimension ranging from about 1 nm to about 100 nm, which may encapsulate (or include) one or more agents and/or may movably bind to one or more agents. Preferable nano-material carriers are known by those skilled in the art, and may comprise nanoparticles, nanopowder, nanocluster, nanocrystal, nanosphere, nanofiber, nanotube, nanocluster, nanocrystal, nanosphere, nanofiber, nanotube, nanogel, and nanorod. Additionally, examples of the substance constituting the nano-material carrier include poly-(lactide-co-glycolide) (PLGA), polyalkylcyanoacrylate (PACA), polyepsilon-caprolactone (PCL), polylactic acid (PLA), polyethyleneglycol (PEG), poly-N-vinylcaprolactam sodium acrylate, poly-N-isopropylacrylamide and polyvinyl acetate. Further, in an embodiment, the nano-material carrier may be fullerene and may comprise spherical fullerenes (e.g., C60), carbon nanotubes, and fullerene derivatives.

The microparticle carrier may be particles having, for example, the longest dimension ranging from about 100 to about 1000 nm. The microparticles may have any shapes and any forms. Examples of the substance constituting the microparticle carrier include poly-(lactide-co-glycolide) (PLGA), polyalkylcyanoacrylate (PACA), polyepsilon-caprolactone (PCL), polylactic acid (PLA), PLGA, and polyethyleneglycol (PEG).

The biostructural carrier refers to a polymer or a compound in which a large number of units in the biostructural carrier are amino acids and/or saccharides and which may encapsulate (or include) one or more agents and/or may movably bind to one or more agents. Preferable biostructural carriers are known by those skilled in the art, and may comprise sugars, monosaccharides, oligosaccharides, polysaccharides, cyclic polysaccharides, non-cyclic polysaccharides, linear polysaccharides, branched polysaccharides, amino acids, proteins and peptides, and semisynthesized derivatives thereof, such as α-cyclodextrin, β-cyclodextrin, γ-cyclodextrin, methyl β-cyclodextrin, dimethyl-β-cyclodextrin, carboxymethyl-β-cyclodextrin, hydroxypropyl-β-cyclodextrin, sulfobutyl ether-β-cyclodextrin, tri-O-methyl-β-cyclodextrin, glucosyl-β-cyclodextrin, β1,3D glucan, β1,6 glucan, C-reactive protein, conalbumin, lactalbumin, ovalbumin, parvalbumin, serum albumin, technetium TC99m aggregated albumin, human serum albumin (HSA), bovine serum albumin (BSA), recombinant human serum albumin (rHSA), glucose (dextrose), fructose, galactose, xylose, ribose, sucrose, cellulose, cyclodextrin and starch.

The micelle carrier has a micelle structure formed with lipids, any fat-soluble (or lipophilic) molecule, oil, wax, sterol, monoglyceride, diglyceride, triglyceride or phospholipid. Polyalkylene glycols such as polyethylene glycol (PEG); polyamino acids such as polyaspartic acid and polyglutamic acid (PGA); poly-(γ-L-glutamyl glutamine) (PGGA), polyphenyleneoxide (PPO), poly(ε-caprolactone) (PCL), poly-(lactide-co-glycolide) (PLGA) or a diblock copolymer may be comprised.

Further, the carrier may be a conjugate and may comprise a nucleotide linker, non-nucleotide linker or nucleotide/non-nucleotide complex linker, which links between a sense region and an antisense region of a nucleic acid, polyethylene glycol, human serum albumin, or a ligand for a cell receptor capable of inducing the cellular uptake. Additionally, the nucleotide linker may be a linker having 2 or more nucleotides in length or may be a nucleic acid aptamer.

The polynucleotide may further comprise at least one substance selected from pharmaceutically acceptable excipients, pharmaceutical carriers and diluents, and can be prepared, by further adding a diluent, a dispersant, a surfactant, a binder, a lubricant or a mixture thereof, into dosage forms including parenteral dosage forms such as injection dosage forms or into forms suitable for oral cavity, rectum, nasal cavity, local, subcutaneous, vaginal or parenteral administration, or into oral dosage forms such as pills, capsules, granules or tablets, or forms suitable for inhalation or infusion administration.

When the polynucleotide is used as a liquid preparation, the carrier is preferably those sterilized and suitable for the living body, and other common additives such as an antioxidant, a buffer solution and a bacteriostatic agent may be added. Preferable are macromolecules, which are large and are metabolized slowly, such as proteins, polysaccharides, polylactoses, polyglycolic acids, polymeric amino acids, amino acid copolymers, lipid aggregates, hydrogels, inactivated virus particles, and collagens. Further, the carrier may also comprise liquids such as water, a saline solution, sterilized water, a Ringer's solution, a buffered saline solution, an albumin injection solution, a dextrose solution, a maltodextrin solution, glycerol, and ethanol, and also adjuvants such as a wetting agent or an emulsifier, a pH buffering agent, and the like.

The administration means to introduce the pharmaceutical composition for treating cancers comprising, as an active ingredient, the polynucleotide to a patient by any suitable method, and includes the delivery of the polynucleotide by a viral or non-viral technique or the transplantation of cells which express the polynucleotide.

The administration can be carried out via various oral or parenteral administration routes as long as the composition can reach a target tissue. For example, the administration can be carried out by an oral, intrarectal, local, intravenous, intraperitoneal, intramuscular, intraarterial, transdermal, intranasal, inhalation, intraocular or intradermal route.

The dose varies depending on the purpose of administration, administration method, type and size of a tumor, conditions (sex, age and body weight, etc.) of a target person to be administered (i.e., a subject). Typically, a drug dose is administered in a lower level and increased until the intended effect is achieved. A preferable dose of the polynucleotide may range, for example, from 1 pmol to 100 nmol per kg of body weight, from 0.001 to 0.25 mg per kg of body weight, from 0.01 to 20 µg per kg of body weight, from 0.10 to 5 µg per kg of body weight, but not limited thereto. Such doses are administered preferably 1 to 10 times, and more preferably 5 to 10 times.

<Suppression of Cancers by Polynucleotide>

The polynucleotide may be provided in any form that it is introduced into cells. The term "introduced into cells" means introducing an exogenous polynucleotide into cells by transfection or transduction. The transfection means that, for example, calcium phosphate-DNA coprecipitation method, DEAE-dextran-mediated transfection method, polybrene-mediated transfection method, electroporation method, microinjection method, liposome fusion method, Lipofectamine transfection and protoplast fusion method, and the transduction means the transfer of a gene into other cells by means of infection using a virus or a virus vector particle (a vector comprising, e.g., adenovirus, adeno-associated virus, Sendai virus or retrovirus (e.g., lentivirus)) or using a plasmid vector. The vector can comprise necessary elements (e.g., promoter) for enabling the expression of the polynucleotide of the present invention and can be prepared by known techniques (e.g., Sambrook and Russell, Molecular Cloning A Laboratory Manual (4$^{th}$ Ed., 2001), Cold Spring Harbor Laboratory Press, JP Patent Publication (Kokai) No. 2016-153403, and JP Patent Publication (Kokai) No. 2016-025853). The cells into which the polynucleotide is introduced by such methods can express the nucleotide sequence at a high level and be thereby utilized as a cell-therapeutic agent for suppressing the growth of a cancer when transplanted into a cancer tissue.

<Type of Cancer>

Tumors and cancers in the present invention mean malignant neoplasms and are used interchangeably. Examples of the cancers to be targeted include, but are not particularly limited to, solid cancers, for example, cancers and cancer cells in the bladder, bone, bone marrow, brain, breast, colon/rectum, esophagus, digestive tract, gum, head, kidney, liver, lung, nasopharynx, neck, ovary, prostate, skin, stomach, testicle, tongue, blood or uterus. Preferably, examples include breast cancer, kidney cancer, pancreatic cancer, colorectal cancer, lung cancer, brain tumor, stomach cancer, cervical cancer, uterine cancer, ovarian cancer, prostate cancer, bladder cancer, esophagus cancer, liver cancer, fibrosarcoma, mast cell tumor and melanoma. These specific cancers include, but are not limited thereto, for example, mammary gland cancer, complex mammary gland cancer, mammary gland malignant mixed tumor, intraductal papillary adenocarcinoma, lung adenocarcinoma, squamous cell carcinoma, small cell carcinoma, large cell carcinoma, glioma which is neuroepithelial tissue tumor, ependymoma, neurocytoma, embryonal neuroectodermal tumor, schwannoma, neurofibroma, meningioma, chronic lymphocytic leukemia, lymphoma, GI lymphoma, digestive lymphoma, small to medium cell lymphoma, cecal cancer, ascending colon cancer, descending colon cancer, transverse colon cancer, sigmoid colon cancer, rectal cancer, epithelial ovarian cancer, germ cell tumor, stromal cell tumor, pancreatic ductal cancer, invasive pancreatic ductal cancer, adenocarcinomas of pancreatic cancer, acinic cell carcinoma, adenosquamous carcinoma, giant cell tumor, intraductal papillary mucinous neoplasm, mucinous cystadenocarcinoma, pancreatoblastoma, serous cystadenocarcinoma, solid papillary cancer, gastrinoma, glucagonoma, insulinoma, multiple endocrine adenomatose, non-functional islet cell tumor, somatostatinoma, and VIPoma. Additionally, examples of the blood cancer include leukemia.

Further, the preferable subjects in the present invention are mammals including primates such as human; livestock such as cow, pig, sheep and horse; companion animals such as dog and cat, and mammals kept in a zoo, preferably human.

<Type of Antitumor Agent>

In the present invention, a drug wherein the pharmaceutical composition for treating and/or preventing cancers comprising, as an active ingredient, the polynucleotide and another antitumor agent (i.e., a pharmaceutical composition comprising another antitumor agent) are combined (referred to as "combination drug"), can be administered in combination to a subject to increase an antitumor effect. The pharmaceutical composition for treating and/or preventing cancers of the present invention and another antitumor agent (i.e., a pharmaceutical composition comprising another antitumor agent) can be administered to a subject simultaneously or separately. For the separate administration, any one of the pharmaceutical compositions may be administered earlier or later, and the dose interval, dose, administration route, and number of doses can be suitably selected by medical specialists. The dosage form of another drug to be administered simultaneously includes, for example, drug compositions obtained by admixing the pharmaceutical composition for treating and/or preventing cancers and the another antitumor agent in a pharmaceutically acceptable carrier (or medium) and preparing them into an intended dosage form (also referred to as "mixed drug").

The antitumor agent includes the following antitumor agents known in literatures and the like.

Examples include, as alkylating agents such as Thiotepa and cyclophosphamide, alkyl sulfonates like (i.e., "such as") Busulfan, improsulfan and piposulfan; aziridines such as benzodopa, carboquone, meturedopa and uredopa; ethyleneimines such as Altretamine, triethyleneamine, triethylenephosphoramide, triethylenethiophosphoramide and trimethylolamine; acetogenins such as bullatacin and bullatacinone; camptothecin; bryostatin; callystatin; cryptophycin 1 and cryptophycin 8; dolastatin; duocarmycin; eleutherobin; pancratistatin; sarcodictyin; spongistatin; Nitrogen mustards such as chlorambucil, chlornaphazine, cholophosphamide and estramustine; ifosfamide; mechlorethamine; mechlorethamine oxide hydrochloride; melphalan; temozolomide; novembichin; fenesterin, prednimustine, trofosfamide; uracil mustard; and nitrosoureas such as bendamustine, carmustine, chlorozotocin, streptozocin, fotemustine, lomustine, nimustine and ranimnustine.

Examples of anticancer antibiotics include calicheamicin, dynemicin, clodronate, esperamicin, aclacinomycin, actinomycin, authramycin, azaserine, bleomycin, cactinomycin, carabicin, carminomycin, carzinophilin, chromomycin, dactinomycin, daunorubicin, detorubicin, 6-diazo-5-oxo-L-norleucine, adriamycin (doxorubicin), bleomycin, aclarbicin, amrubicin, epirubicin, esorubicin, idarubicin, marcellomycin, mitomycin C, mycophenolic acid, nogalamycin, olivomycin, peplomycin, potfiromycin, puromycin, quelamycin, rodorubicin, streptonigrin, streptozocin, tubercidin, ubenimex, zinostatin, and zorubicin.

Examples of antimetabolites include folic acid analogs such as denopterin, pteropterin, methotrexate, trimetrexate and pemetrexed; purine analogs such as fludarabine, 6-mercaptopurine, thiamiprine, thioguanine, cladribine and clofarabine; pyrimidine analogs such as ancitabine, azacitidine, 6-azauridine, carmofur, cytarabine, dideoxyuridine, doxifluridine, enocitabine, floxuridine, trifluridine, capecitabine, 5-FU, gemcitabine, S-1 and tegafur; hydroxycarbamide, and nelarabine.

Examples of hormone preparations include anastrozole, bicalutamide, degarelix, estramustine, exemestane, flutamide, fulvestrant, goserelin, letrozole, leuplin, medroxyprogesterone, mepitiostane, octreotide, tamoxifen and toremifene, for example, androgen preparations such as calusterone, drostanolone propionate, epitiostanol, mepitiostane, testolactone and enzalutamide; antiadrenal preparations such as aminoglutethimid, mitotane and trilostane; frolinic acid, aceglatone, aldophosphamide glycoside, aminolevulinic acid, eniluracil, amsacrine, bestrabucil, bisantrene, edatraxate, defofamine, demecolcine, diaziquone, elformithine, elliptinium acetate, epothilone, etoglucid, lenthinan, lonidamine, maytansine, ansamitocine, abiraterone, mitoguazone, mitoxantrone, mopidanmol, nitraerine, pentostatin, phenamet, pirarubicin, losoxantrone, podophyllic acid, 2-ethyl hydrazide, procarbazine, razoxane, rhizoxin, sizofiran, spirogermanium, tenuazonic acid, triaziquone, Roridin A, anguidine, urethane, vindesine, dacarbazine, mannomustine, mitobronitol, mitolactol, pipobroman, gacytosine, arabinoside, BCG, Krestin and picibanil.

Examples of other anticancer agents such as those derived from plants include docetaxel, etoposide, teniposide, irinotecan, nogitecan, paclitaxel, cabazitaxel, vinblastine, vincristine, vindesine, vinorelbine, carboplatin, cisplatin, dacarbazine, eribulin, L-asparaginase, miriplatin, mitoxantrone, nedaplatin, oxaliplatin, pentostatin, procarbazine, arsenic trioxide, sobuzoxane, tamibarotene, mitoxantrone, novantrone, edatrexate, ibandronate, topoisomerase inhibitor, difluoromethylornithine (DMFO), and retinoic acid.

Examples of molecularly targeted drugs include afatinib, axitinib, alectinib, bevacizumab, cetuximab, crizotinib, erlotinib, everolimus, gefitinib, lapatinib, ramucirumab, panitumumab, pazopanib, pertuzumab, nivolumab, regorafenib, lenvatinib, sorafenib, sunitinib, temsirolimus, and trastuzumab, and pharmaceutically acceptable salts or derivatives thereof.

Further, radioisotopes such as $^{211}At$, $^{131}I$, $^{125}I$, $^{90}Y$, $^{186}Re$, $^{188}Re$, $^{153}Sm$, $^{212}Bi$, $^{32}P$, $^{175}Lu$, $^{176}Lu$, $^{89}Sr$, $^{223}Ra$ and $^{161}Tb$ known in literatures and the like may also be used. Radioisotopes are preferably those effective for treating and diagnosing tumors, and such radioisotopes may also be comprised in the pharmaceutical composition for treating and/or preventing cancers of the present invention.

<Treatment and Prevention Methods>

The present invention further provides a method for treating and/or preventing a cancer in a subject who suffers (or has suffered) from a cancer, comprising administering the pharmaceutical composition for treating and/or preventing cancers of the present invention, or a combination drug comprising the pharmaceutical composition and another antitumor in combination, to the subject.

The term "prevention" as used herein includes the prevention of cancer recurrence for reducing a risk of recurrence after cancer treatment by cancer therapy such as surgery, chemotherapy, radiotherapy or immunotherapy.

For the pharmaceutical composition, the combination drug, the polynucleotide which is the active ingredient, the dosage, the usage, the preparation form, and the type of cancers to be targeted, the contents described above similarly apply in this section.

EXAMPLES

The present invention is further specifically described in reference to the following Examples. However, the scope of the present invention shall not be limited to these Examples.

Example 1

Effectiveness of Synthetic RNAs on Pancreatic Cancer Cells

The synthetic RNA having the same nucleotide sequence as hsa-miR-6893-5p represented by SEQ ID NO: 7, the synthetic RNA having the same nucleotide sequence as hsa-miR-4476 represented by SEQ ID NO: 8, the synthetic RNA having the same nucleotide sequence as hsa-miR-6808-5p represented by SEQ ID NO: 9, and the synthetic RNA having the same nucleotide sequence as hsa-miR-6876-5p represented by SEQ ID NO: 10 were evaluated, respectively, for the effectiveness on pancreatic cancer cells.

Panc-1 cell line (ATCC) cells as the pancreatic cancer cells were seeded in DMEM medium (nacalai tesque, Japan) containing 10% FBS and were cultured under conditions of 37° C. and 5% $CO_2$. $6 \times 10^3$ cells were seeded per well of 96-well plates, and RNA synthetic products (Thermo Fisher Scientific Inc. mirVana™ miRNA Mimics) having the nucleotide sequences represented by SEQ ID NOs: 7, 8, 9 and 10 or the negative control oligo (Thermo Fisher Scientific Inc. mirVana™ miRNA Mimic, Negative Control) at a concentration of 30 nM, respectively, were gene-transferred using Lipofectamine RNAiMAX (Thermo Fisher Scientific Inc.). Culture solution was exchanged 24 hours later and the number of cells was counted for 5 days. The number of cells was determined by measuring ATP activity using the Celtiter-glo (Promega Corporation) reagent and was used as viable cell counts. The measurement was carried out in n=3 and the graphs are presented in mean±standard deviation.

As a result, the pancreatic cancer cells into which the RNA synthetic products having the nucleotide sequences represented by SEQ ID NOs: 7, 8, 9 and 10 were gene-transferred, respectively, had cell viabilities of 50%, 51%, 39% and 50%, respectively, when compared with the pancreatic cancer cells into which the negative control oligo was transferred. The results are shown in FIG. 1.

Example 2

Effectiveness of Synthetic RNAs on Breast Cancer Cells

The synthetic RNA having the same nucleotide sequence as hsa-miR-6893-5p represented by SEQ ID NO: 7, the synthetic RNA having the same nucleotide sequence as hsa-miR-4476 represented by SEQ ID NO: 8, the synthetic RNA having the same nucleotide sequence as hsa-miR-6808-5p represented by SEQ ID NO: 9, and the synthetic RNA having the same nucleotide sequence as hsa-miR-6876-5p represented by SEQ ID NO: 10 were evaluated, respectively, for the effectiveness on breast cancer cells.

MCF-7 cell line (ATCC) cells as the breast cancer cells were seeded in RPMI medium (nacalai tesque, Japan) containing 10% FBS and were cultured under conditions of 37° C. and 5% $CO_2$. $6 \times 10^3$ cells were seeded per well of 96-well plates, and RNA synthetic products (Thermo Fisher Scientific Inc. mirVana™ miRNA Mimics) having the nucleotide sequences represented by SEQ ID NOs: 7, 8, 9 and 10 or the negative control oligo (Thermo Fisher Scientific Inc. mirVana™ miRNA Mimic, Negative Control) at a concentration of 30 nM, respectively, were gene-transferred using Lipofectamine RNAiMAX (Thermo Fisher Scientific Inc.). Culture solution was exchanged 24 hours later and the number of cells was counted for 5 days. The number of cells was determined by measuring ATP activity using the Celtiter-glo (Promega Corporation) reagent and was used as viable cell counts. The measurement was carried out in n=3 and the graphs are presented in mean±standard deviation.

Figure 2:
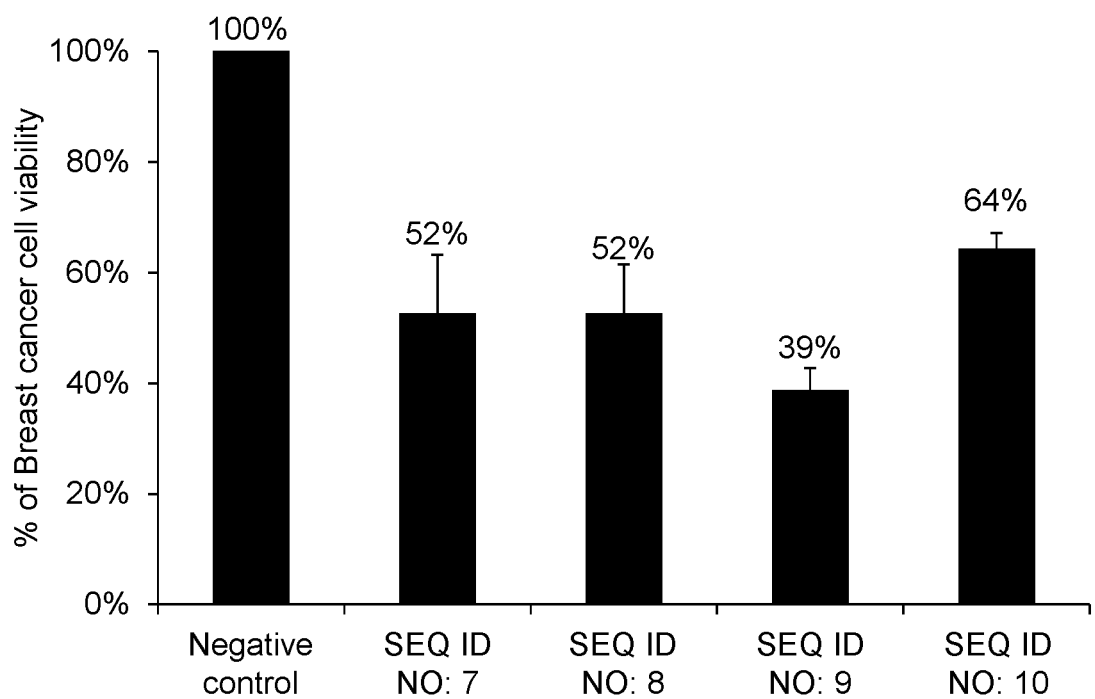
FIG. 2 shows percentages, relative to the viable cell count (100%) of breast cancer cell line MCF-7 after transferring the negative control oligo as a synthetic RNA, of the viable cell counts after transferring a synthetic RNA having the same nucleotide sequence as hsa-miR-6893-5p represented by SEQ ID NO: 7, a synthetic RNA having the same nucleotide sequence as hsa-miR-4476 represented by SEQ ID NO: 8, a synthetic RNA having the same nucleotide sequence as hsa-miR-6808-5p represented by SEQ ID NO: 9, and a synthetic RNA having the same nucleotide sequence as hsa-miR-6876-5p represented by SEQ ID NO: 10.

As a result, the breast cancer cells into which the RNA synthetic products having the nucleotide sequences represented by SEQ ID NOs: 7, 8, 9 and 10 were gene-transferred, respectively, had cell viabilities of 52%, 52%, 39% and 64%, respectively, when compared with the breast cancer cells into which the negative control oligo was transferred. The results are shown in FIG. 2.

Example 3

Effectiveness of Synthetic RNAs on Lung Cancer Cells

The synthetic RNA having the same nucleotide sequence as hsa-miR-6893-5p represented by SEQ ID NO: 7, the synthetic RNA having the same nucleotide sequence as hsa-miR-4476 represented by SEQ ID NO: 8, the synthetic RNA having the same nucleotide sequence as hsa-miR-6808-5p represented by SEQ ID NO: 9, and the synthetic RNA having the same nucleotide sequence as hsa-miR-6876-5p represented by SEQ ID NO: 10 were evaluated, respectively, for the effectiveness on lung cancer cells.

A549 cell line (ATCC) cells as the lung cancer cells were seeded in RPMI medium (nacalai tesque, Japan) containing 10% FBS and were cultured under conditions of 37° C. and 5% $CO_2$. $3 \times 10^3$ cells were seeded per well of 96-well plates, and RNA synthetic products (Thermo Fisher Scientific Inc. mirVana™ miRNA Mimics) having the nucleotide sequences represented by SEQ ID NOs: 7, 8, 9 and 10 or the negative control oligo (Thermo Fisher Scientific Inc. mirVana™ miRNA Mimic, Negative Control) at a concentration of 30 nM, respectively, were gene-transferred using Lipofectamine RNAiMAX (Thermo Fisher Scientific Inc.). Culture solution was exchanged 24 hours later and the number of cells was counted for 5 days. The number of cells was determined by measuring ATP activity using the Celtiter-glo (Promega Corporation) reagent and was used as viable cell counts. The measurement was carried out in n=3 and the graphs are presented in mean±standard deviation.

Figure 3:
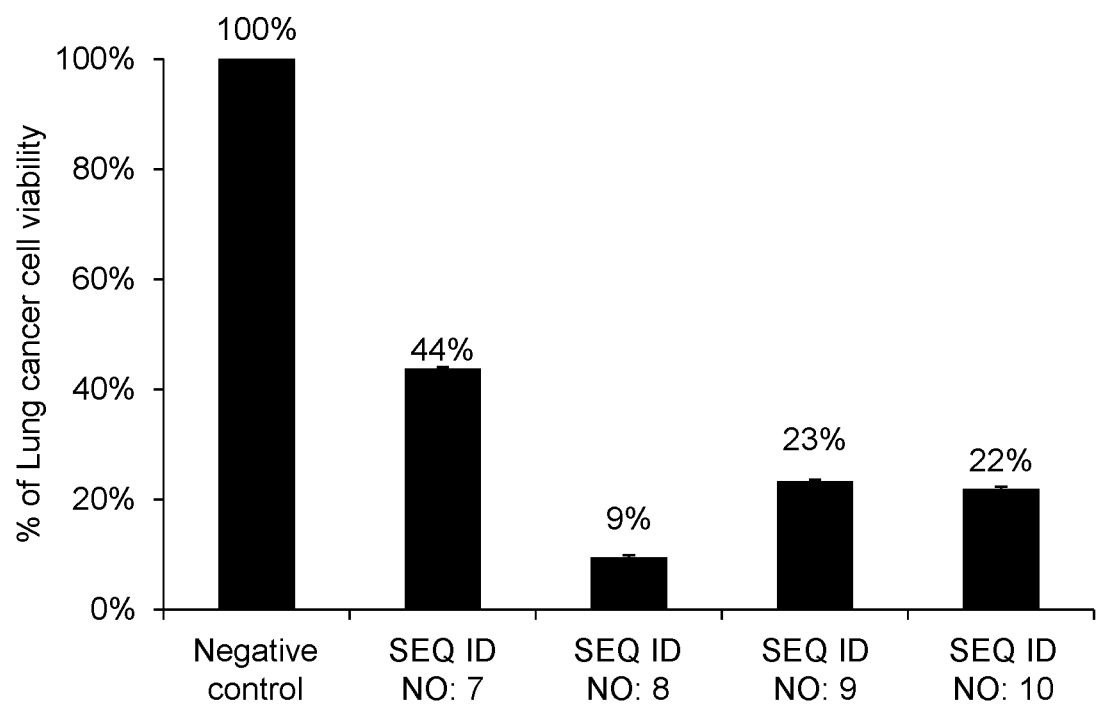
FIG. 3 shows percentages, relative to the viable cell count (100%) of lung cancer cell line A549 after transferring the negative control oligo as a synthetic RNA, of the viable cell counts after transferring a synthetic RNA having the same nucleotide sequence as hsa-miR-6893-5p represented by SEQ ID NO: 7, a synthetic RNA having the same nucleotide sequence as hsa-miR-4476 represented by SEQ ID NO: 8, a synthetic RNA having the same nucleotide sequence as hsa-miR-6808-5p represented by SEQ ID NO: 9, and a synthetic RNA having the same nucleotide sequence as hsa-miR-6876-5p represented by SEQ ID NO: 10.

As a result, the lung cancer cells into which the RNA synthetic products having the nucleotide sequences represented by SEQ ID NOs: 7, 8, 9 and 10 were gene-transferred, respectively, had cell viabilities of 44%, 9%, 23% and 22%, respectively, when compared with the lung cancer cells into which the negative control oligo was transferred. The results are shown in FIG. 3.

Example 4

Effectiveness of Synthetic RNAs on Stomach Cancer Cells

The synthetic RNA having the same nucleotide sequence as hsa-miR-6893-5p represented by SEQ ID NO: 7, the synthetic RNA having the same nucleotide sequence as hsa-miR-4476 represented by SEQ ID NO: 8, the synthetic RNA having the same nucleotide sequence as hsa-miR-6808-5p represented by SEQ ID NO: 9, and the synthetic RNA having the same nucleotide sequence as hsa-miR-6876-5p represented by SEQ ID NO: 10 were evaluated respectively for the effectiveness on stomach cancer cells.

NCI-N87 cell line (ATCC) cells as the stomach cancer cells were seeded in RPMI medium (nacalai tesque, Japan) containing 10% FBS and were cultured under conditions of 37° C. and 5% $CO_2$. $3 \times 10^3$ cells were seeded per well of 96-well plates, and RNA synthetic products (Thermo Fisher Scientific Inc. mirVana™ miRNA Mimics) having the nucleotide sequences represented by SEQ ID NOs: 7, 8, 9 and 10 or the negative control oligo (Thermo Fisher Scientific Inc. mirVana™ miRNA Mimic, Negative Control) at a concentration of 30 nM, respectively, were gene-transferred using Lipofectamine RNAiMAX (Thermo Fisher Scientific Inc.). Culture solution was exchanged 24 hours later and the number of cells was counted for 5 days. The number of cells was determined by measuring ATP activity using a Celtiter-glo (Promega Corporation) reagent and was used as viable cell counts. The measurement was carried out in n=3 and the graphs are presented in mean±standard deviation.

Figure 4:
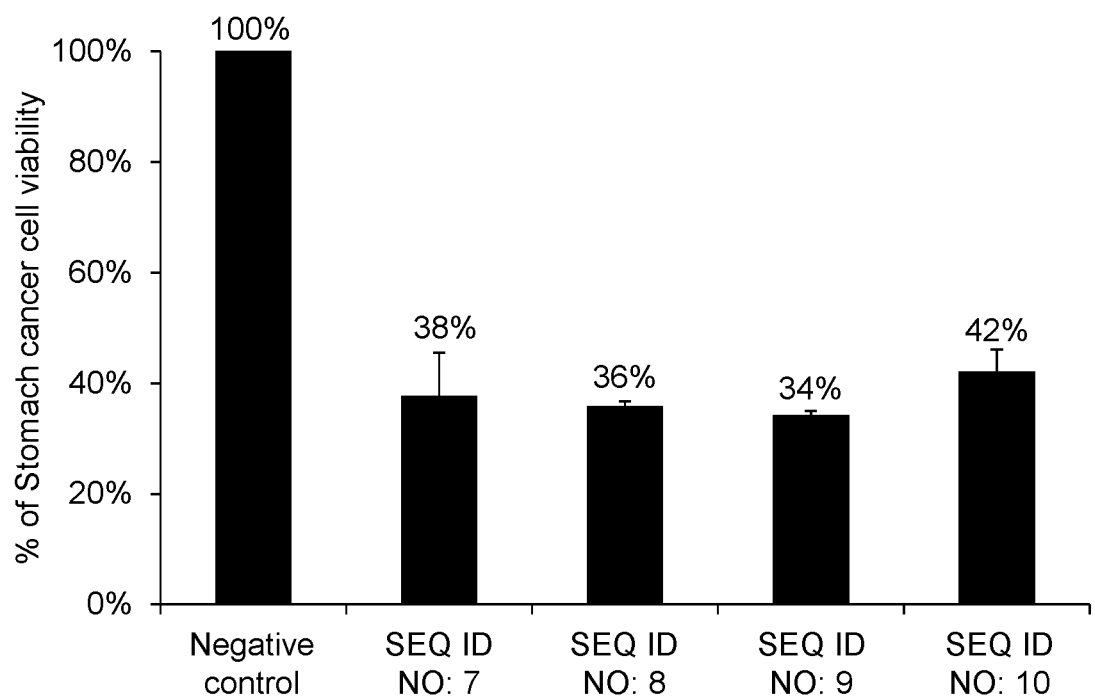
FIG. 4 shows percentages, relative to the viable cell count (100%) of stomach cancer cell line NC1-N87 after transferring the negative control oligo as a synthetic RNA, of the viable cell counts after transferring a synthetic RNA having the same nucleotide sequence as hsa-miR-6893-5p represented by SEQ ID NO: 7, a synthetic RNA having the same nucleotide sequence as hsa-miR-4476 represented by SEQ ID NO: 8, a synthetic RNA having the same nucleotide sequence as hsa-miR-6808-5p represented by SEQ ID NO: 9, and a synthetic RNA having the same nucleotide sequence as hsa-miR-6876-5p represented by SEQ ID NO: 10.

As a result, the stomach cancer cells into which the RNA synthetic products having the nucleotide sequences represented by SEQ ID NOs: 7, 8, 9 and 10 were gene-transferred, respectively, had cell viabilities of 38%, 36%, 34% and 42%, respectively. The results are shown in FIG. 4.

Example 5

Effectiveness of Synthetic RNAs on Liver Cancer Cells

The synthetic RNA having the same nucleotide sequence as hsa-miR-6893-5p represented by SEQ ID NO: 7, the synthetic RNA having the same nucleotide sequence as hsa-miR-4476 represented by SEQ ID NO: 8, the synthetic RNA having the same nucleotide sequence as hsa-miR-6808-5p represented by SEQ ID NO: 9, and the synthetic RNA having the same nucleotide sequence as hsa-miR-6876-5p represented by SEQ ID NO: 10 were evaluated, respectively, for the effectiveness on liver cancer cells.

HEPG2 cell line (ATCC) cells as the liver cancer cells were seeded in RPMI medium (nacalai tesque, Japan) containing 10% FBS and incubated under conditions of 37° C. and 5% $CO_2$. $6 \times 10^3$ cells were seeded per well of a 96-well plate, and RNA synthetic products (Thermo Fisher Scientific Inc. mirVana™ miRNA Mimics) having the nucleotide sequences represented by SEQ ID NOs: 7, 8, 9 and 10 or the negative control oligo (Thermo Fisher Scientific Inc. mirVana™ miRNA Mimic, Negative Control) at a concentration of 30 nM, respectively, were gene-transferred using Lipofectamine RNAiMAX (Thermo Fisher Scientific Inc.). Culture solution was exchanged 24 hours later and the number of cells was counted for 5 days. The number of cells was determined by measuring ATP activity using the Celtiter-glo (Promega Corporation) reagent and was used as viable cell counts. The measurement was carried out in n=3 and the graphs are presented in mean±standard deviation.

Figure 5:
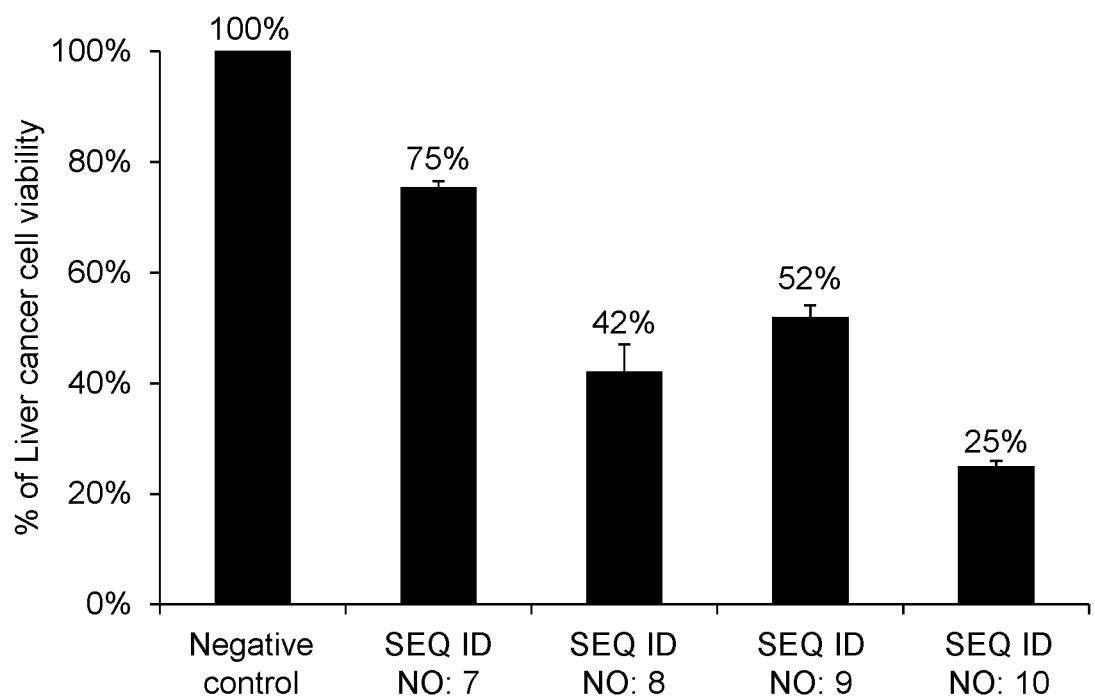
FIG. 5 shows percentages, relative to the viable cell count (100%) of liver cancer cell line HepG2 after transferring the negative control oligo as a synthetic RNA, of the viable cell counts after transferring a synthetic RNA having the same nucleotide sequence as hsa-miR-6893-5p represented by SEQ ID NO: 7, a synthetic RNA having the same nucleotide sequence as hsa-miR-4476 represented by SEQ ID NO: 8, a synthetic RNA having the same nucleotide sequence as hsa-miR-6808-5p represented by SEQ ID NO: 9, and a synthetic RNA having the same nucleotide sequence as hsa-miR-6876-5p represented by SEQ ID NO: 10.

As a result, the liver cancer cells into which the RNA synthetic products having the nucleotide sequences represented by SEQ ID NOs: 7, 8, 9 and 10 were gene-transferred, respectively, had cell viabilities of 75%, 42%, 52% and 25%, respectively. The results are shown in FIG. 5.

Example 6

Effectiveness of Synthetic RNA on Leukemia Cells

The synthetic RNA having the same nucleotide sequence as hsa-miR-4476 represented by SEQ ID NO: 8 was evaluated for the effectiveness on leukemia cells.

JURKAT cell line (ATCC) cells as the leukemia cells were seeded in RPMI medium (nacalai tesque, Japan) containing 10% FBS and were cultured under conditions of 37° C. and 5% $CO_2$. $4 \times 10^4$ cells were seeded per well of 96-well plates, and an antisense RNA (Thermo Fisher Scientific Inc. mirVana™ miRNA Inhibitors) or the negative control oligo (Thermo Fisher Scientific Inc., mirVana™ miRNA Inhibitor, Negative Control) at a concentration of 30 nM was gene-transferred using Viromer (Lipocalyx GmbH). The number of cells was counted for 5 days. The number of cells was determined by measuring the ATP activity using the Celtiter-glo (Promega Corporation) reagent and was used as viable cell counts. The measurement was carried out in n=3 and the graphs are presented in mean±standard deviation.

Figure 6:
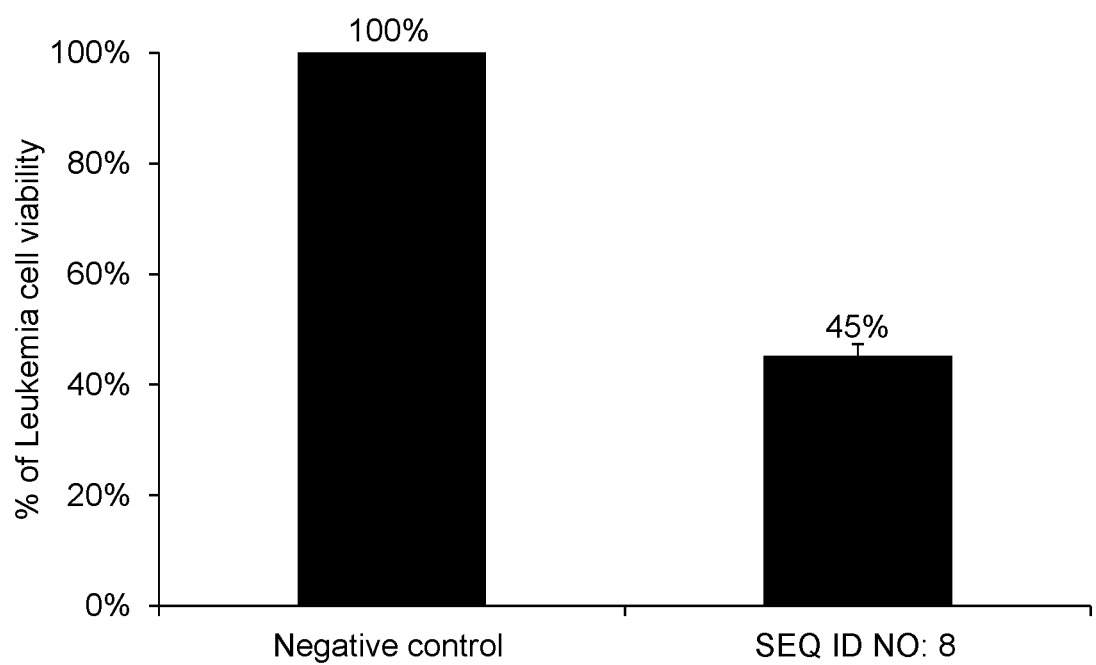
FIG. 6 shows a percentage, relative to the viable cell count (100%) of leukemia cell line Jurkat after transferring the negative control oligo as a synthetic RNA, of the viable cell counts after transferring a synthetic RNA having the same nucleotide sequence as hsa-miR-4476 represented by SEQ ID NO: 8.

As a result, the cell viability of the leukemia cells into which the synthetic RNA represented by SEQ ID NO: 8 was gene-transferred was 45%. The results are shown in FIG. 6.

Example 7

Effectiveness of Synthetic RNAs on Colorectal Cancer Cells (1)

The synthetic RNA having the same nucleotide sequence as hsa-miR-6893-5p represented by SEQ ID NO: 7, the synthetic RNA having the same nucleotide sequence as hsa-miR-4476 represented by SEQ ID NO: 8, the synthetic RNA having the same nucleotide sequence as hsa-miR-6808-5p represented by SEQ ID NO: 9, and the synthetic RNA having the same nucleotide sequence as hsa-miR-6876-5p represented by SEQ ID NO: 10 were evaluated, respectively, for the effectiveness on colorectal cancer cells.

HCT116 cell line (ATCC) cells as the colorectal cancer cells were seeded in McCoy's medium (nacalai tesque, Japan) containing 10% FBS and were cultured under conditions of 37° C. and 5% $CO_2$. $6 \times 10^3$ cells were seeded per well of a 96-well plate, and RNA synthetic products (Thermo Fisher Scientific Inc. mirVana™ miRNA Mimics) having the nucleotide sequences represented by SEQ ID NOs: 7, 8, 9 and 10 or the negative control oligo (Thermo Fisher Scientific Inc., mirVana™ miRNA Mimic, Negative Control) at a concentration of 30 nM, respectively, were gene-transferred using Lipofectamine RNAiMAX (Thermo Fisher Scientific Inc.). Culture solution was exchanged 24 hours later and the number of cells was counted for 5 days. The number of cells was determined by measuring ATP activity using the Celtiter-glo (Promega Corporation) reagent and was used as viable cell counts. The measurement was carried out in n=3 and the graphs are presented in mean±standard deviation.

Figure 7:
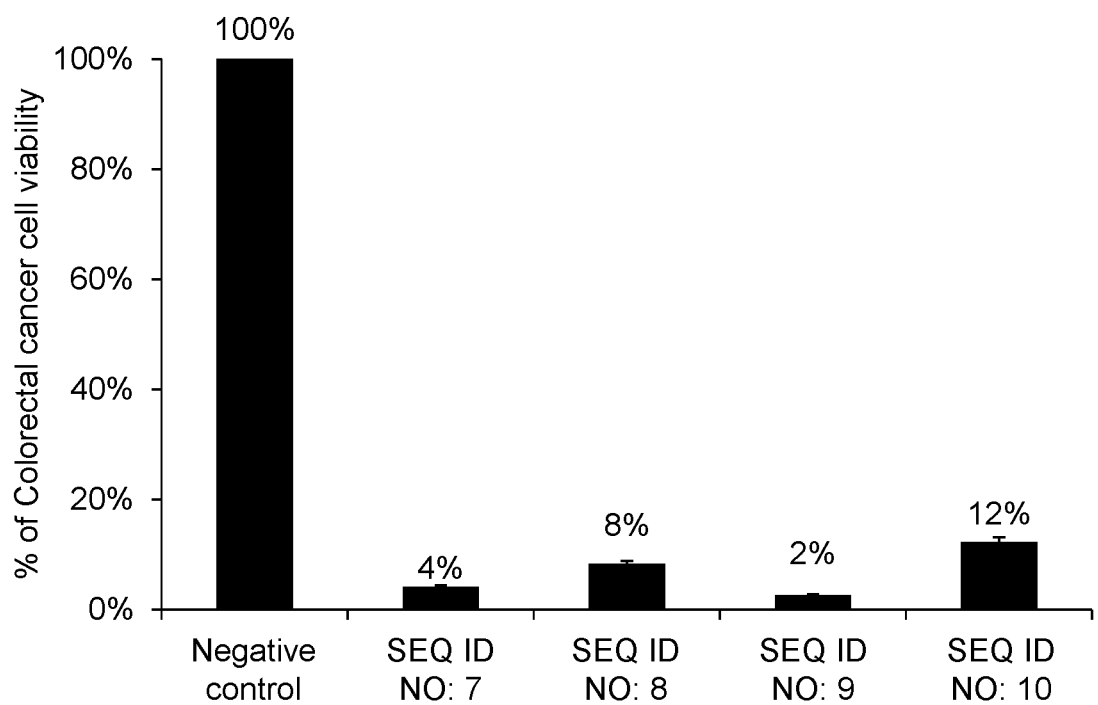
FIG. 7 shows percentages, relative to the viable cell count (100%) of colorectal cancer cell line HCT116 after transferring the negative control oligo as a synthetic RNA, of the viable cell counts after transferring a synthetic RNA having the same nucleotide sequence as hsa-miR-6893-5p represented by SEQ ID NO: 7, a synthetic RNA having the same nucleotide sequence as hsa-miR-4476 represented by SEQ ID NO: 8, a synthetic RNA having the same nucleotide sequence as hsa-miR-6808-5p represented by SEQ ID NO: 9, and a synthetic RNA having the same nucleotide sequence as hsa-miR-6876-5p represented by SEQ ID NO: 10.

As a result, the colorectal cancer cells into which the RNA synthetic products having the nucleotide sequences represented by SEQ ID NOs: 7, 8, 9 and 10 were gene transferred, respectively, had cell viabilities of 4%, 8%, 2% and 12%, respectively, when compared with the colorectal cancer cells into which the negative control oligo was transferred. The results are shown in FIG. 7.

Example 8

Effectiveness of Synthetic RNAs on Colorectal Cancer Cells (2)

A synthetic RNA having the same nucleotide sequence as hsa-miR-4454 represented by SEQ ID NO: 11 known as a cancer marker, a synthetic RNA having the nucleotide sequence represented by SEQ ID NO: 12 (which is the nucleotide sequence wherein the nucleotide sequence (SEQ ID NO: 16) of from the 9th to the 20th nucleotides from the 5' terminal side of hsa-miR-4454 represented by SEQ ID NO: 11 was added to the 3' terminal side of SEQ ID NO: 2 or to the nucleotide sequence of from the 1st to the 8th nucleotides from the 5' terminal side of SEQ ID NO: 8), and a synthetic RNA (Thermo Fisher Scientific Inc., mirVana™ miRNA Mimics) having the nucleotide sequence represented by SEQ ID NO: 13 (which is the nucleotide sequence wherein the nucleotide sequence of SEQ ID NO: 3, or the nucleotide sequence from the 9th to the 21st nucleotides from the 5' terminal side, of SEQ ID NO: 7, was added to the 3' terminal side of SEQ ID NO: 2) were evaluated for the effectiveness on colorectal cancer according to the method described in Example 7.

Figure 8:
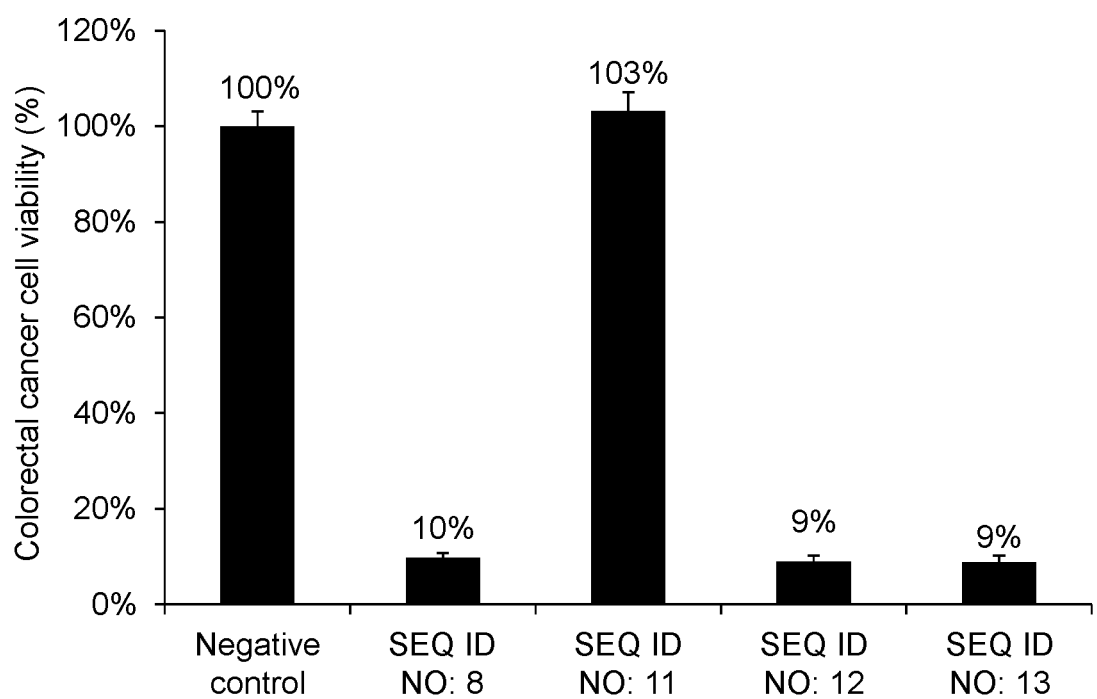
FIG. 8 shows percentages, relative to the viable cell count (100%) of colorectal cancer cell line HCT116 after transferring the negative control oligo as a synthetic RNA, of the viable cell counts after transferring a synthetic RNA (the present invention) having the same nucleotide sequence as hsa-miR-4476 represented by SEQ ID NO: 8, a synthetic RNA having the same nucleotide sequence represented by SEQ ID NO: 12 (the preset invention), a synthetic RNA having the same nucleotide sequence represented by SEQ ID NO: 13 (the present invention), and a synthetic RNA having the same nucleotide sequence as hsa-miR-4454 represented by SEQ ID NO: 11 (comparative example).

As a result, the colorectal cancer cells into which the RNA synthetic products having the nucleotide sequences represented by SEQ ID NOs: 8, 12 and 13 were gene-transferred had cell viabilities not more than 10%, whereas the colorectal cancer cells into which the RNA synthetic product having the nucleotide sequence represented by SEQ ID NO: 11 was gene-transferred had a cell viability of 103%, revealing that this synthetic RNA was not substantially effective. The results are shown in FIG. 8.

Comparative Example 1

Effectiveness of Synthetic RNAs on Colorectal Cancer Cell

A synthetic RNA having the same nucleotide sequence as hsa-miR-575 represented by SEQ ID NO: 14 known as a cancer marker and a synthetic RNA (Thermo Fisher Scientific Inc., mirVana™ miRNA Mimics) having the same nucleotide sequence as hsa-miR-1321 represented by SEQ ID NO: 15 (where the nucleotide sequence from the 1st to 8th nucleotides from the 5' terminal side has a sequence identity of 87.5% with the nucleotide sequences represented by SEQ ID NOs: 1 and 2) known to be associated with blood cancer treatment, were evaluated for the effectiveness on colorectal cancer according to the method described in Example 7.

Figure 9:
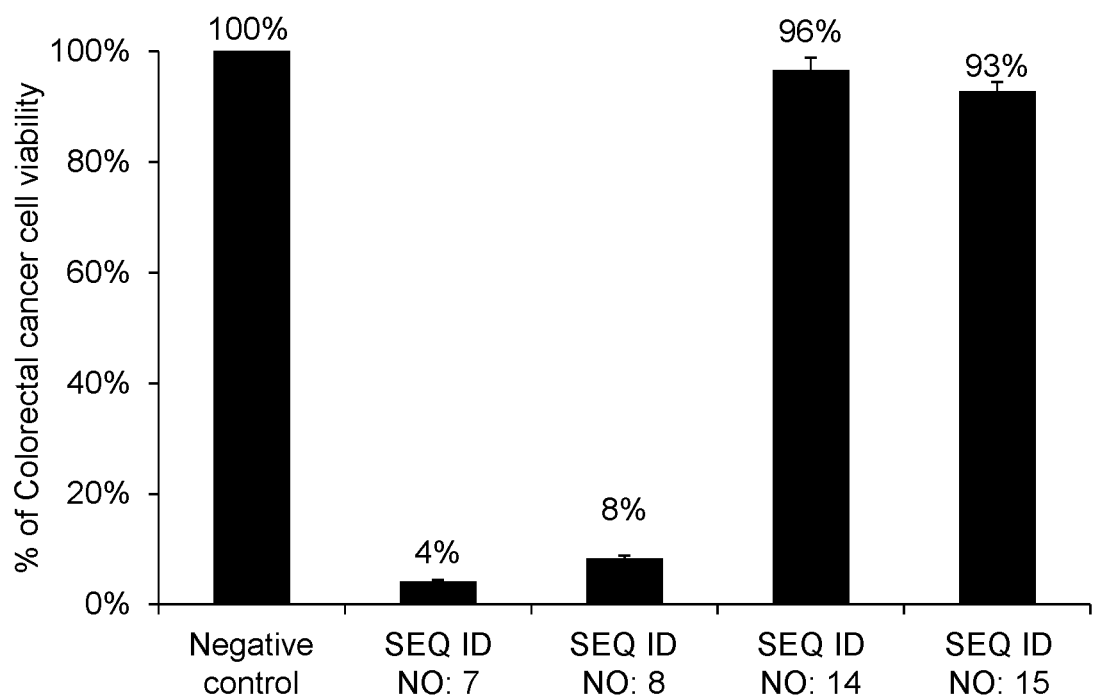
FIG. 9 shows percentages, relative to the viable cell count (100%) of colorectal cancer cell line HCT116 after transferring the negative control oligo as a synthetic RNA, of the viable cell counts after transferring a synthetic RNA (the present invention) having the same nucleotide sequence as hsa-miR-6893-5p represented by SEQ ID NO: 7, a synthetic RNA having the same nucleotide sequence as hsa-miR-4476 represented by SEQ ID NO: 8 (the preset invention), a synthetic RNA having the same nucleotide sequence as hsa-miR-575 represented by SEQ ID NO: 14 (comparative example), and a synthetic RNA having the same nucleotide sequence as hsa-miR-1321 represented by SEQ ID NO: 15 (comparative example).

As a result, the colorectal cancer cells into which the RNA synthetic products having the nucleotide sequences represented by SEQ ID NOs: 7 and 8 were gene-transferred, respectively, had cell viabilities not more than 10%, whereas the colorectal cancer cells into which the RNA synthetic products having the nucleotide sequences represented by SEQ ID NOs: 14 and 15 were gene-transferred, respectively, had cell viabilities of 96% and 93%, respectively, revealing that these synthetic RNAs were not substantially effective. The results are shown in FIG. 9.

Comparative Example 2

Effectiveness of Synthetic RNAs on Normal Cell

Synthetic RNAs (Thermo Fisher Scientific Inc., mir-Vana™ miRNA Mimics) having the nucleotide sequences represented by SEQ ID NO: 7 and SEQ ID NO: 8 were evaluated for the effectiveness on mammary epithelial cells and pulmonary microvascular endothelial cells, both of which are normal cells.

184B5 (ATCC) cells, as the mammary epithelial cells, were seeded in MEBM medium (Lonza) containing BPE, hydrocortisone, hEGF and insulin and were cultured under conditions of 37° C. and 5% $CO_2$. $6 \times 10^3$ cells were seeded per well of 96-well plates, and RNA synthetic products having the nucleotide sequences represented by SEQ ID NO: 7 and SEQ ID NO: 8 or the negative control oligo (Thermo Fisher Scientific Inc., mirVana™ miRNA Mimic, Negative Control) at a concentration of 3 nM, respectively, were gene-transferred using Lipofectamine RNAiMAX (Thermo Fisher Scientific Inc.). Culture solution was exchanged 24 hours later and the number of cells was counted for 5 days. The number of cells was determined by measuring ATP activity using the Celtiter-glo (Promega Corporation) reagent and was used as viable cell counts. The measurement was carried out in n=3 and the graphs are presented in mean±standard deviation.

Figure 10:
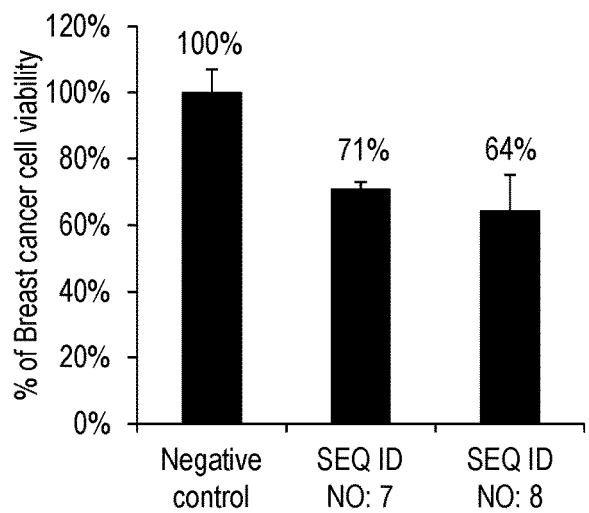
FIG. 10 shows: (A) percentages, relative to the viable cell count (100%) of breast cancer cell line MCF-7 after transferring the negative control oligo as a synthetic RNA; (B) percentages, relative to the viable cell count (100%) of mammary epithelial cell line 184B5, which are normal cells after, transferring the negative control oligo as a synthetic RNA; and (C) percentages, relative to the viable cell count (100%) of pulmonary microvascular endothelial cell line HMVEC-L, which are normal cells, after transferring the negative control oligo as a synthetic RNA, of the viable cell counts of the respective cell lines after transferring the synthetic RNA having the same nucleotide sequence as hsa-miR-6893-5p represented by SEQ ID NO: 7 and a synthetic RNA having the same nucleotide sequence as hsa-miR-4476 represented by SEQ ID NO: 8 (each 3 nM).
Figure 10:
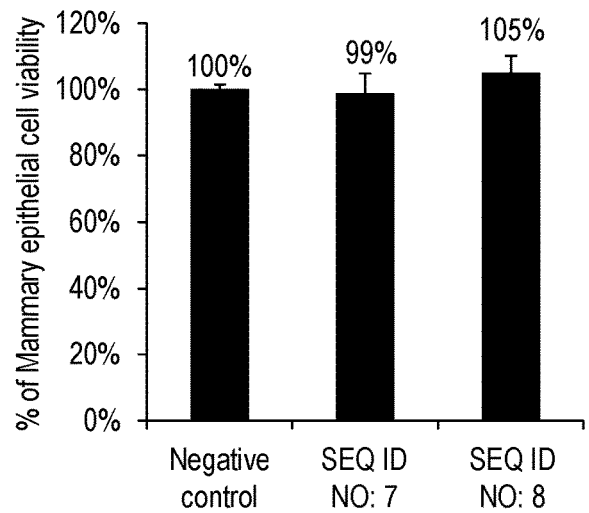
Figure 10:
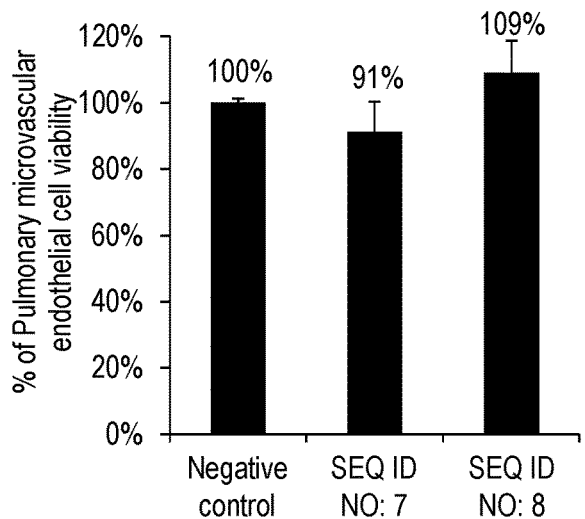

As a result, the breast cancer cells MCF-7 into which the RNA synthetic products (3 nM each) having the nucleotide sequences represented by SEQ ID NO: 7 and SEQ ID NO: 8 were gene-transferred had cell viabilities of 71% and 64%, respectively, (FIG. 10A), whereas mammary epithelial cells had cell viabilities of 99% and 105%, respectively, revealing that the synthetic RNAs did not affect the normal cells (FIG. 10B).

Further, HMVEC-L (ATCC) cells, as the pulmonary microvascular endothelial cells, were seeded in EGM-2 medium (Lonza) containing EGM-2MV SigleQuots (Lonza) and were cultured under conditions of 37° C. and 5% $CO_2$. $6 \times 10^3$ cells were seeded per well of 96-well plates, and RNA synthetic products having the nucleotide sequences represented by SEQ ID NO: 7 and SEQ ID NO: 8 or the negative control oligo at a concentration of 3 nM, respectively, were gene transferred using Lipofectamine RNAiMAX. Culture solution was exchanged 24 hours later and the number of cells was counted for 5 days. The number of cells was determined by measuring ATP activity using the Celtiter-glo reagent and was used as viable cell counts. The measurement was carried out in n=3 and the graphs are presented in mean±standard deviation.

As a result, the pulmonary microvascular endothelial cells had cell viabilities of 91% and 109%, respectively, revealing that the synthetic RNAs did not affect the normal cells (FIG. 10C).

Example 9

Effectiveness of Synthetic RNA on Cancer-Bearing Model Mouse

Using cancer-bearing mice into which a human-derived cancer cell line was transplanted, a synthetic RNA having the same nucleotide sequence as hsa-miR-4476 represented by SEQ ID NO: 8 was studied on antitumor effect.

To the back of 6 Balb/c nude mice (Charles River Japan Inc.), $5 \times 10^6$ cells of human colorectal cancer cell line HCT116 (ATCC) per animal were subcutaneously transplanted and were allowed to grow until the diameter of the tumor reached about 5 mm. To each of the 6 cancer-bearing mice, a mixed solution of 50 μl of 0.5% Atelocollagen (KOKEN CO., LTD.) and 2 nmol of a synthetic RNA having the same nucleotide sequence as SEQ ID NO: 8 or the negative control per animal was subcutaneously administered around the tumor. Subsequently, every 2 days, 3 times in total, the mixed solution of 0.5% Atelocollagen and each synthetic RNA was subcutaneously administered in the same dose around the tumor of each cancer-bearing mouse, and the size of the tumor was measured once every two days. The size of the tumor was calculated as the volume using the formula of 0.5× (long diameter×short diameter×short diameter).

Figure 11:
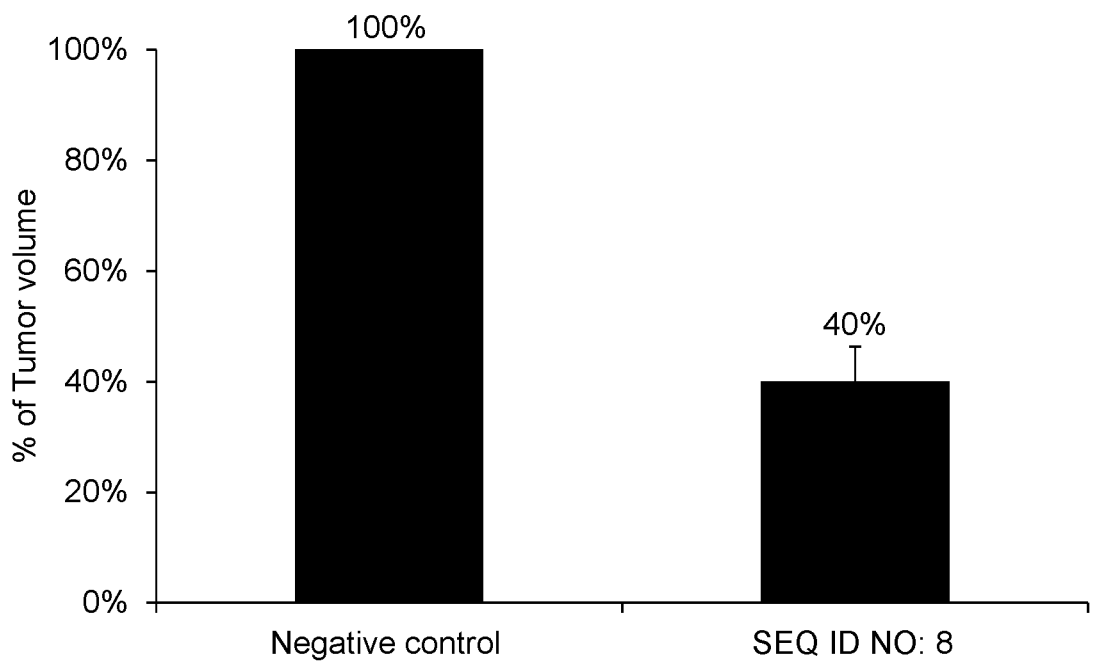
FIG. 11 shows (B) the change in tumor volume for 13 days and (A) the % of tumor volume on Day 13 after the synthetic RNA having the same nucleotide sequence as hsa-miR-4476 represented by SEQ ID NO: 8 and the negative control oligo as a synthetic RNA were administered to tumor-bearing mice, respectively.
Figure 11:
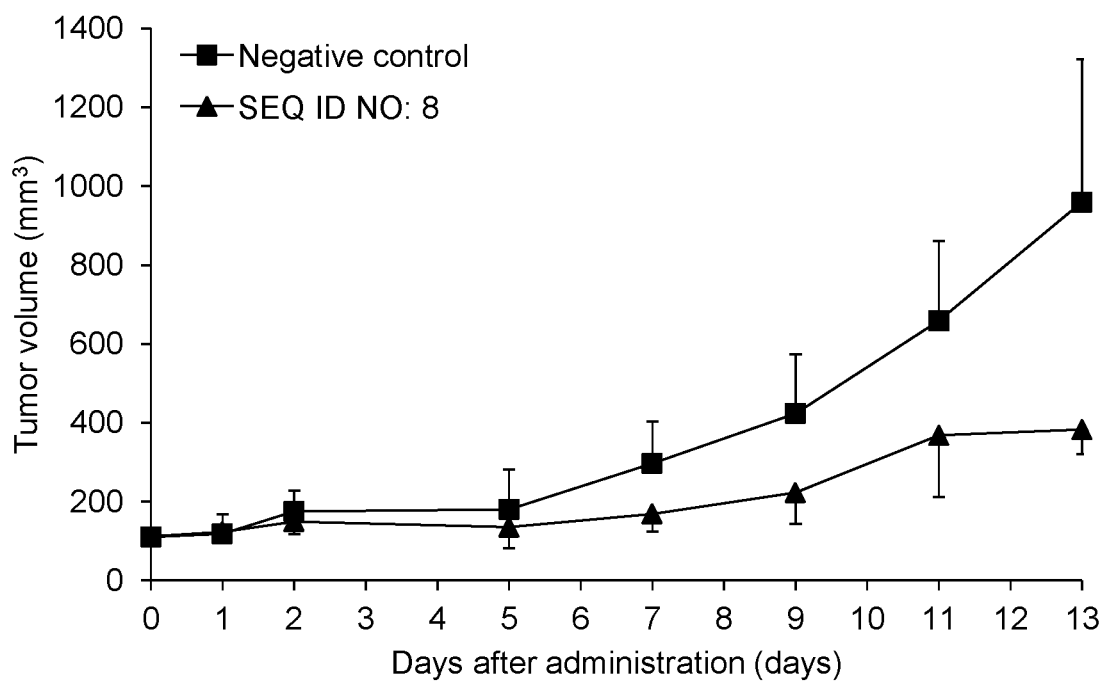

As a result, on Day 13 from the initial administration, the % of tumor volume of the test group to which the synthetic RNA having the same nucleotide sequence as SEQ ID NO: 8 was administered was 40% when the control group was 100% (FIG. 11A). Additionally, the change in e tumor volume for 13 days after the administration of the synthetic RNA to the cancer-bearing mice is shown in FIG. 11B. The results show that the synthetic RNA having the same nucleotide sequence as SEQ ID NO: 8 exhibits the in vivo antitumor effect on the colorectal cancer cells.

INDUSTRIAL APPLICABILITY

The pharmaceutical composition for treating cancers of the present invention is useful to treat and/or prevent cancers.

All publications, patents and patent applications cited herein are incorporated herein by reference in their entirety.

The invention claimed is:

1. A method for treating a cancer in a subject in need thereof, comprising administering to the subject a pharmaceutical composition comprising, as an active ingredient, a polynucleotide 20-22 nucleotides in length and comprising a nucleotide sequence of any of SEQ ID NOs: 3 to 6 and 16 at the 3' terminal side of the nucleotide sequence of SEQ ID NO:1 or 2; and wherein the cancer is selected from the group consisting of breast cancer, lung cancer, stomach cancer, liver cancer, colorectal cancer, pancreatic cancer, and leukemia.

2. The method according to claim 1, wherein the polynucleotide comprises a nucleotide sequence of any of SEQ ID NOs:7 to 10, 12 and 13.

3. The method according to claim 1, wherein the polynucleotide is single stranded or double stranded.

4. The method according to claim 1, wherein the polynucleotide is RNA.

5. The method according to claim 1, wherein the polynucleotide is inserted expressibly in a vector in the form of DNA.

6. The method according to claim 1, wherein the polynucleotide is encapsulated in a carrier selected from the group consisting of non-cationic polymer carriers, liposome carriers, dendritic carriers, nano-material carriers, microparticle carriers, biostructural carriers, micelle carriers, polymer microparticles, and magnetic fine particles, or is bound thereto.

7. The method according to claim 1, wherein the pharmaceutical composition is simultaneously or separately administered to a subject in combination with an antitumor agent.

* * * * *

SEQUENCE LISTING

<160> NUMBER OF SEQ ID NOS: 16

<210> SEQ ID NO 1
<211> LENGTH: 8
<212> TYPE: RNA
<213> ORGANISM: Homo sapiens

<400> SEQUENCE: 1 caggcagg                                                              8

-continued

```
<210> SEQ ID NO 2
<211> LENGTH: 8
<212> TYPE: RNA
<213> ORGANISM: Homo sapiens

<400> SEQUENCE: 2 caggaagg                                                                  8

<210> SEQ ID NO 3
<211> LENGTH: 13
<212> TYPE: RNA
<213> ORGANISM: Homo sapiens

<400> SEQUENCE: 3
uguagggugg agc                                                           13

<210> SEQ ID NO 4
<211> LENGTH: 14
<212> TYPE: RNA
<213> ORGANISM: Homo sapiens

<400> SEQUENCE: 4
auuuagggac aggc                                                          14

<210> SEQ ID NO 5
<211> LENGTH: 14
<212> TYPE: RNA
<213> ORGANISM: Homo sapiens

<400> SEQUENCE: 5 gagguggggac caug                                                         14

<210> SEQ ID NO 6
<211> LENGTH: 14
<212> TYPE: RNA
<213> ORGANISM: Homo sapiens

<400> SEQUENCE: 6
agacaggcag uuca                                                          14

<210> SEQ ID NO 7
<211> LENGTH: 21
<212> TYPE: RNA
<213> ORGANISM: Homo sapiens

<400> SEQUENCE: 7
caggcaggug uagggguggag c                                                 21

<210> SEQ ID NO 8
<211> LENGTH: 22
<212> TYPE: RNA
<213> ORGANISM: Homo sapiens

<400> SEQUENCE: 8
caggaaggau uuagggacag gc                                                 22

<210> SEQ ID NO 9
<211> LENGTH: 22
<212> TYPE: RNA
<213> ORGANISM: Homo sapiens

<400> SEQUENCE: 9
caggcaggga ggugggacca ug                                                 22
```

```
<210> SEQ ID NO 10
<211> LENGTH: 22
<212> TYPE: RNA
<213> ORGANISM: Homo sapiens

<400> SEQUENCE: 10
caggaaggag acaggcaguu ca                                              22

<210> SEQ ID NO 11
<211> LENGTH: 20
<212> TYPE: RNA
<213> ORGANISM: Homo sapiens

<400> SEQUENCE: 11
ggauccgagu cacggcacca                                                 20

<210> SEQ ID NO 12
<211> LENGTH: 20
<212> TYPE: RNA
<213> ORGANISM: Homo sapiens

<400> SEQUENCE: 12
caggaagggu cacggcacca                                                 20

<210> SEQ ID NO 13
<211> LENGTH: 21
<212> TYPE: RNA
<213> ORGANISM: Homo sapiens

<400> SEQUENCE: 13
caggaaggug uaggguggag c                                               21

<210> SEQ ID NO 14
<211> LENGTH: 19
<212> TYPE: RNA
<213> ORGANISM: Homo sapiens

<400> SEQUENCE: 14
gagccaguug gacaggagc                                                  19

<210> SEQ ID NO 15
<211> LENGTH: 18
<212> TYPE: RNA
<213> ORGANISM: Homo sapiens

<400> SEQUENCE: 15
cagggaggug aaugugau                                                   18

<210> SEQ ID NO 16
<211> LENGTH: 12
<212> TYPE: RNA
<213> ORGANISM: Homo sapiens

<400> SEQUENCE: 16
gucacggcac ca                                                         12
```